United States Patent [19]
Sugiyama et al.

[11] Patent Number: 5,787,866
[45] Date of Patent: Aug. 4, 1998

[54] AIR-FUEL RATIO SENSOR

[75] Inventors: Tomio Sugiyama, Nagoya; Naoto Miwa, Tsushima; Hiromi Sano; Masahiro Shibata, both of Nagoya; Syuichi Nakano; Shinichiro Imamura, both of Kariya, all of Japan

[73] Assignee: Denso Corporation, Kariya, Japan

[21] Appl. No.: 833,801

[22] Filed: Apr. 9, 1997

[30] Foreign Application Priority Data

Apr. 12, 1996 [JP] Japan ................. 8-115825

[51] Int. Cl.[6] ............................................. B05D 5/12
[52] U.S. Cl. ....................... 123/672; 204/426; 427/344
[58] Field of Search ........................... 204/425, 426, 204/427; 427/343, 344; 123/672

[56] References Cited

U.S. PATENT DOCUMENTS

| | | | |
|---|---|---|---|
| 4,107,019 | 8/1978 | Takao et al. | 204/425 |
| 4,345,985 | 8/1982 | Tohda et al. | 204/425 |
| 4,462,890 | 7/1984 | Touda et al. | 204/425 |
| 4,464,244 | 8/1984 | Uchida et al. | 204/425 |
| 4,498,968 | 2/1985 | Yamada et al. | 204/425 |
| 4,510,036 | 4/1985 | Takeuchi et al. | 204/425 |
| 4,559,126 | 12/1985 | Mase et al. | 204/425 |
| 4,658,790 | 4/1987 | Kitahara | 123/693 |
| 4,697,165 | 9/1987 | Ishiguro et al. | |
| 4,755,274 | 7/1988 | Mase et al. | 204/425 |
| 4,785,150 | 11/1988 | Kojima et al. | |
| 4,814,059 | 3/1989 | Nishizawa et al. | 204/406 |
| 4,857,275 | 8/1989 | Furusaki et al. | 422/98 |
| 4,883,947 | 11/1989 | Murase et al. | |
| 4,909,922 | 3/1990 | Kata et al. | 204/406 |
| 4,958,514 | 9/1990 | Takami et al. | 73/25.03 |
| 5,028,309 | 7/1991 | Nishizawa et al. | 204/425 |
| 5,676,811 | 10/1997 | Makino et al. | 204/425 |

FOREIGN PATENT DOCUMENTS

| | | |
|---|---|---|
| 61-109289 | 5/1985 | Japan . |
| 61-138487 | 6/1985 | Japan . |
| 60-212986 | 10/1985 | Japan . |
| 1-231285 | 9/1989 | Japan . |
| 5-034313 | 2/1993 | Japan . |

Primary Examiner—David A. Okonsky
Attorney, Agent, or Firm—Cushman Darby & Cushman IP Group of Pillsbury Madison & Sutro LLP

[57] ABSTRACT

An air-fuel ratio sensor comprises a platelike oxygen sensing section made of a solid electrolyte and a heater sheet heating the oxygen sensing section. The oxygen sensing section and the heater sheet are stacked via spacers to constitute a multilayer construction. The heater sheet comprises a first platelike insulating sheet chiefly containing at least one component selected from the group consisting of α-alumina, steatite and mullite, a filmy resistance element disposed on the first insulating sheet and having a resistance-temperature coefficient within a range of $0.5 \times 10^3$ to $2.0 \times 10^3$ ppm/°C., and a second platelike insulating sheet covering the resistance element and chiefly containing at least one component selected from the group consisting of α-alumina, steatite and mullite.

15 Claims, 8 Drawing Sheets

AIR-FUEL RATIO SENSOR

BACKGROUND OF THE INVENTION

1. Field of the Invention

This invention relates to an air-fuel ratio sensor having laminated platelike layers comprising an oxygen sensing element portion and a heater portion, and more particularly to an air-fuel ratio sensor excellent in both warmup ability and durability.

2. Related Art

An inadequate setting of an air-fuel ratio in an internal combustion engine will lead to bad fuel economy of an automotive vehicle and may cause air pollution. To avoid this, the air-fuel ratio of an internal combustion engine is detected by an air-fuel ratio sensor that is normally installed in an exhaust passage to detect an oxygen concentration of exhaust gas emitted from the combustion chamber of the engine. A fuel injection amount is feedback controlled based on an output of the air-fuel ratio sensor to adequately adjust the air-fuel ratio of gas mixture introduced into the combustion chamber. Usually, air-fuel ratio sensors are active in a high-temperature atmosphere equivalent to the temperature of exhaust gas in an ordinary operating condition of a well warmed-up engine. In an engine startup condition, the temperature of exhaust gas is not satisfactorily high. Air-fuel ratio sensors are not heated so quickly during the startup operation due to their large heat capacities. Unsatisfactorily activated air-fuel ratio sensors cannot accurately detect the concentration of an intended exhaust gas component. This is not desirable in avoiding deterioration of fuel economy and generation of air pollution. Therefore, there is a necessity of rapidly and forcibly increasing the temperature of the air-fuel ratio sensor.

However, increasing the temperature of an air-fuel ratio sensor so rapidly may cause a crack in the solid electrolyte body. This possibly shortens the life of the air-fuel ratio sensor.

SUMMARY OF THE INVENTION

A principal object of the present invention is to provide an air-fuel ratio sensor having excellent warmup ability and sufficient durability.

In order to accomplish above-described and other related objects, the present invention provides an air-fuel ratio sensor comprising a platelike oxygen sensing section made of a solid electrolyte, and a heater sheet heating the oxygen sensing section. The oxygen sensing section and the heater sheet are stacked with intervening spacers to constitute a multilayer construction. Furthermore, the heater sheet comprises a filmy resistance element interposed between first and second platelike insulating sheets. The first platelike insulating sheet chiefly contains at least one component selected from the group consisting of α-alumina, steatite and mullite. The filmy resistance element, disposed on the first insulating sheet, has a resistance-temperature coefficient within a range of $0.5 \times 10^3$ to $2.0 \times 10^3$ ppm/°C. The second platelike insulating sheet covers the resistance element and chiefly contains at least one component selected from the group consisting of α-alumina, steatite and mullite.

Preferably, to improve ease of fabrication, the resistance element of the air-fuel ratio sensor of the present invention is made of a cermet comprising a primary component of Pt and a secondary component selected from the group consisting of Rh, Pd and Ir.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

A basic technological background of the present invention will be explained hereinafter with reference to FIGS. 10 and 11.

Figure 10:
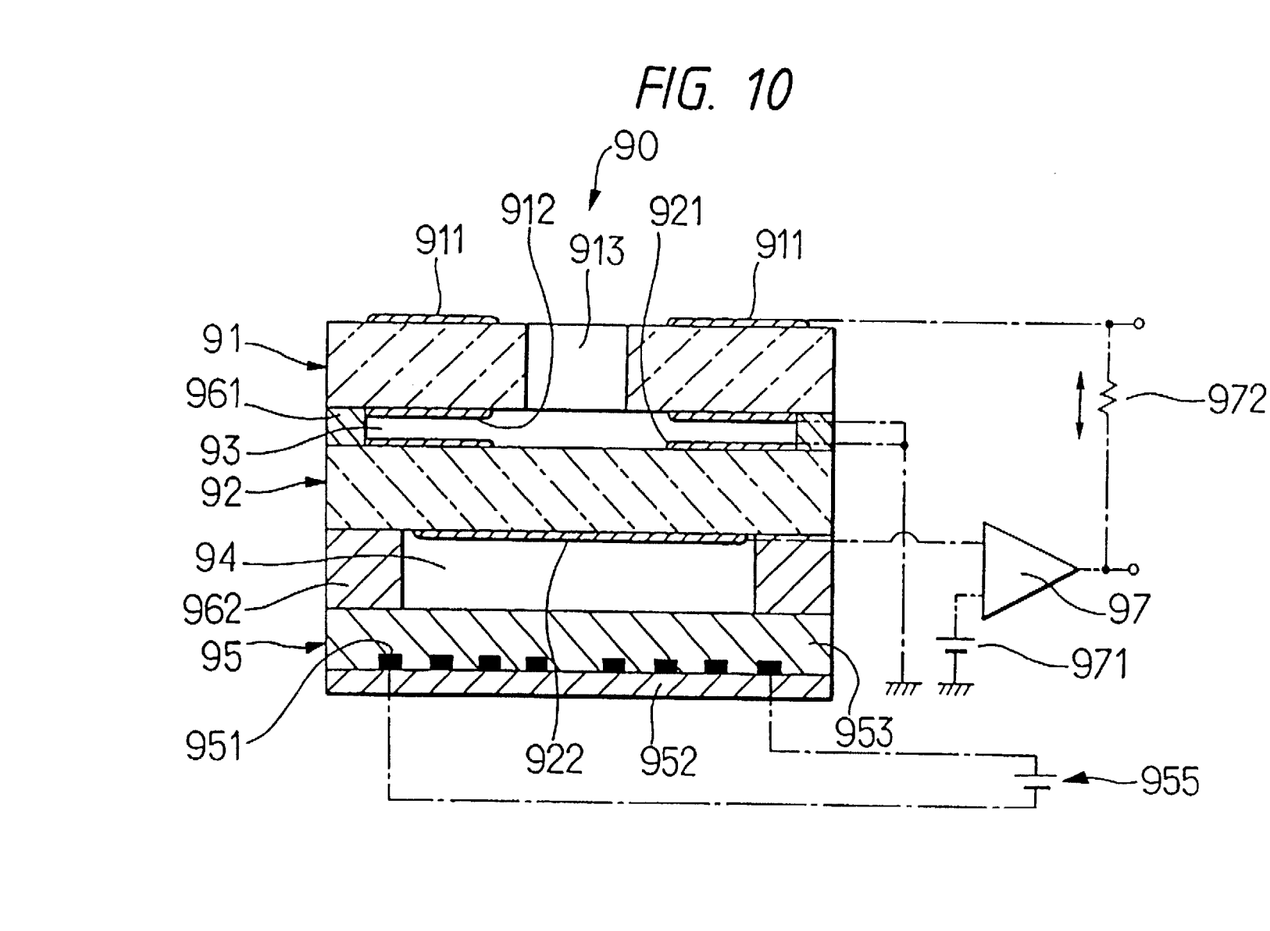
FIG. 10 is a transverse cross-sectional view showing constituents of the comparative air-fuel ratio sensor.
Figure 11:
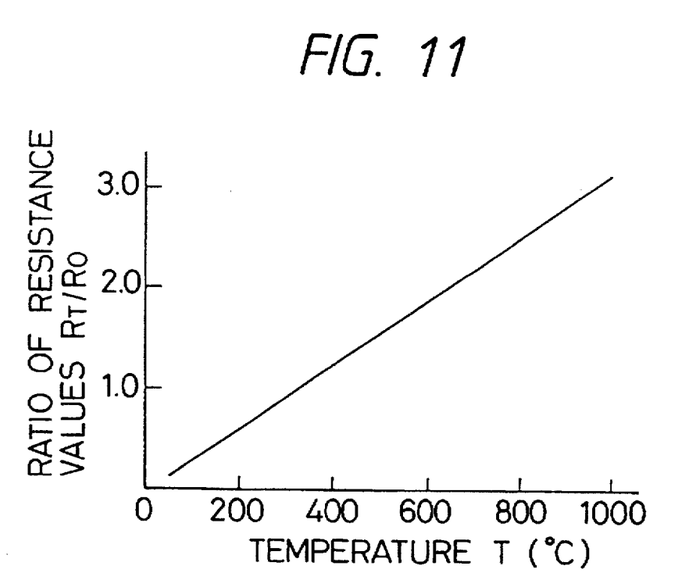
FIG. 11 is a graph showing a resistance change of a resistance element in accordance with a temperature change in the comparative air-fuel ratio sensor.

FIG. 10 shows a multilayer type air-fuel ratio sensor 90 comprising an oxygen pumping cell 91 disposed at one side, an oxygen sensing cell 92 disposed inwardly of the oxygen pumping cell 91, a measured gas chamber 93 defined between oxygen pumping cell 91 and oxygen sensing cell 92, and a referential gas chamber 94 defined behind the oxygen sensing cell 92. The oxygen pumping cell 91 comprises a platelike body sheet made of a zirconia group solid electrolyte. A porous electrode 911 is attached on an outer surface of the platelike body sheet. A porous electrode 912 is attached on an inner surface of the platelike body sheet. The oxygen sensing cell 92 comprises a platelike body sheet made of a zirconia group solid electrolyte. A porous electrode 921 is attached on one surface closer to the oxygen pumping cell 91. A porous electrode 922 is attached on the opposite surface. The oxygen sensing cell 92 causes electrochemical reaction in accordance with the partial pressure of its environmental oxygen.

The measured gas chamber 93 is communicated via a gas diffusion control section 913 to an outside space filled with the measured gas. Oxygen pumping cell 91 has a function of pumping oxygen into the measured gas chamber 93 as well as a function of pumping out the same to the outside space. The oxygen sensing cell 92 detects the oxygenic partial pressure in the measured gas chamber 93 in comparison with that of the referential gas chamber 94 filled with atmospheric air.

A heater sheet 95, comprising a resistance element 951, is disposed closely to the referential chamber 94 at a side opposed to the oxygen sensing cell 92. The heater sheet 95 has a function of promptly warming up the sensor body and maintaining the sensor temperature at a predetermined higher level. Upon an electric power source 955 supplying electric power to the resistance element 951, the heater sheet 95 generates heat and increases the temperature of neighboring components, such as electrodes 911 and 912 of oxygen pumping cell 91 and electrodes 921 and 922 of oxygen sensing cell 92.

The resistance element 951 is made of a cermet of Pt-group alloy and alumina. The resistance element 951 is filmy and formed on an insulating sheet 952 of alumina. Another insulating sheet 953 of alumina is provided on the resistance element 951 so as to surround the resistance element 951 hermetically by alumina. The air-fuel ratio sensor 90 controls the temperature of the element in response to a variation of the resistance value of resistance element 951, for example, with reference to a relationship shown in FIG. 11. In FIG. 11, Ro represents a resistance value at a room temperature and RT represents a resistance value at a temperature T.

In FIG. 10, reference numeral 961 represents an alumina sheet with an opening defining the measured gas chamber 93. Reference numeral 962 represents another alumina sheet with an opening defining the referential gas chamber 94. Reference numeral 97 represents an amplifier 97 amplifying a detection signal. Reference numeral 971 represents a referential voltage source that determines an input level of the amplifier 97. Reference numeral 972 represents a partial-potential resistance that adjusts the level of an applied voltage.

Figure 8:
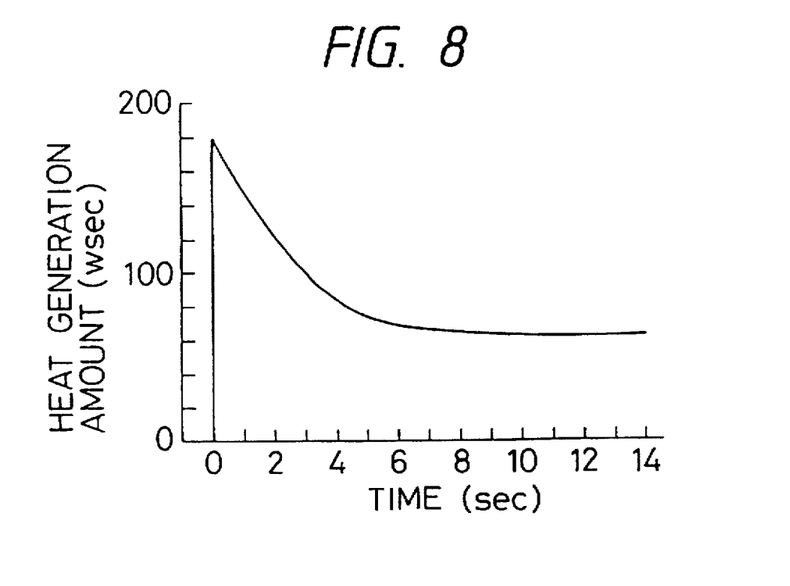
Fig.8 is a view showing a change in the heat generation for a comparative air-fuel ratio sensor.

Pt, serving as a heater member for the resistance element 951 in the air-fuel ratio sensor 90, has a resistance-temperature coefficient of approximately $3.1 \times 10^3$ ppm/°C. The resistance value of the resistance element 951 changes due to self heat generation as shown in FIG. 11. When a constant voltage is applied, a heat generation amount changes in reverse proportion to the resistance value as shown in FIG. 8. The air-fuel ratio sensor 90 is heated by this resistance element 951, and the temperature of this air-fuel ratio sensor 90 increases as shown in FIG. 9.

Figure 9:
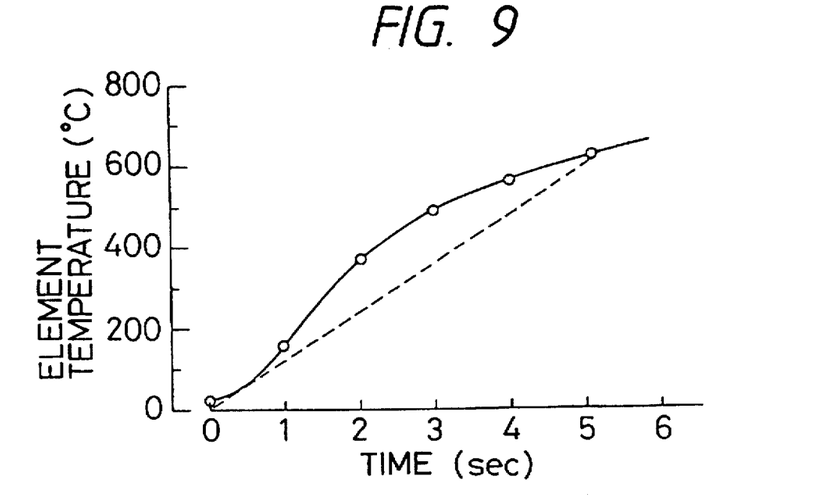
FIG. 9 is a view showing a temperature change of the comparative air-fuel ratio sensor.

As apparent from FIG. 9, the temperature gradient (°C/sec) is variable depending on an elapsed time during the temperature increase of the sensor element. The sensor element and the heater sheet are subjected to a thermal stress proportional to this temperature gradient. The generated thermal stress may exceed the strength limit of respective sensor constituents, especially insulating sheets 952 and 953 in the heat generating section. This is not desirable and may reduce the durability of insulating sheets 952 and 953.

Air-fuel ratio sensors used for automotive vehicles are required to improve their warmup ability to satisfy severe regulations imposed on exhaust gas emissions. Especially, promptly activating the air-fuel ratio sensor in an engine startup operation is important and a key to clear the recent severe regulations. More specifically, during an engine startup operation, there is a tendency that a relatively large amount of harmful emission containing HC (hydrocarbon) is exhausted from the engine. In view of the near-future severe regulations to be imposed on HC, it is believed that air-fuel ratio sensors need to be activated within five seconds after starting engines.

To this end, the above-described multilayer type air-fuel ratio sensor is advantageous for its excellent heat conductive ability between the heater and the reaction portion.

For the multilayer type air-fuel ratio sensor 90 shown in FIG. 10, an active temperature is about 600° C. at which the sensor starts ordinary operation.

In view of the foregoing, causing a 600° C. temperature increase within a short time of five seconds with no cracks of the elements (e.g., insulating sheets 952 and 953) is a goal to be achieved by the present invention.

Preferred embodiments of the present invention will be explained hereinafter with reference to accompanied drawings. Identical parts are denoted by the same reference numerals throughout the drawings.

First Embodiment

Figure 1:
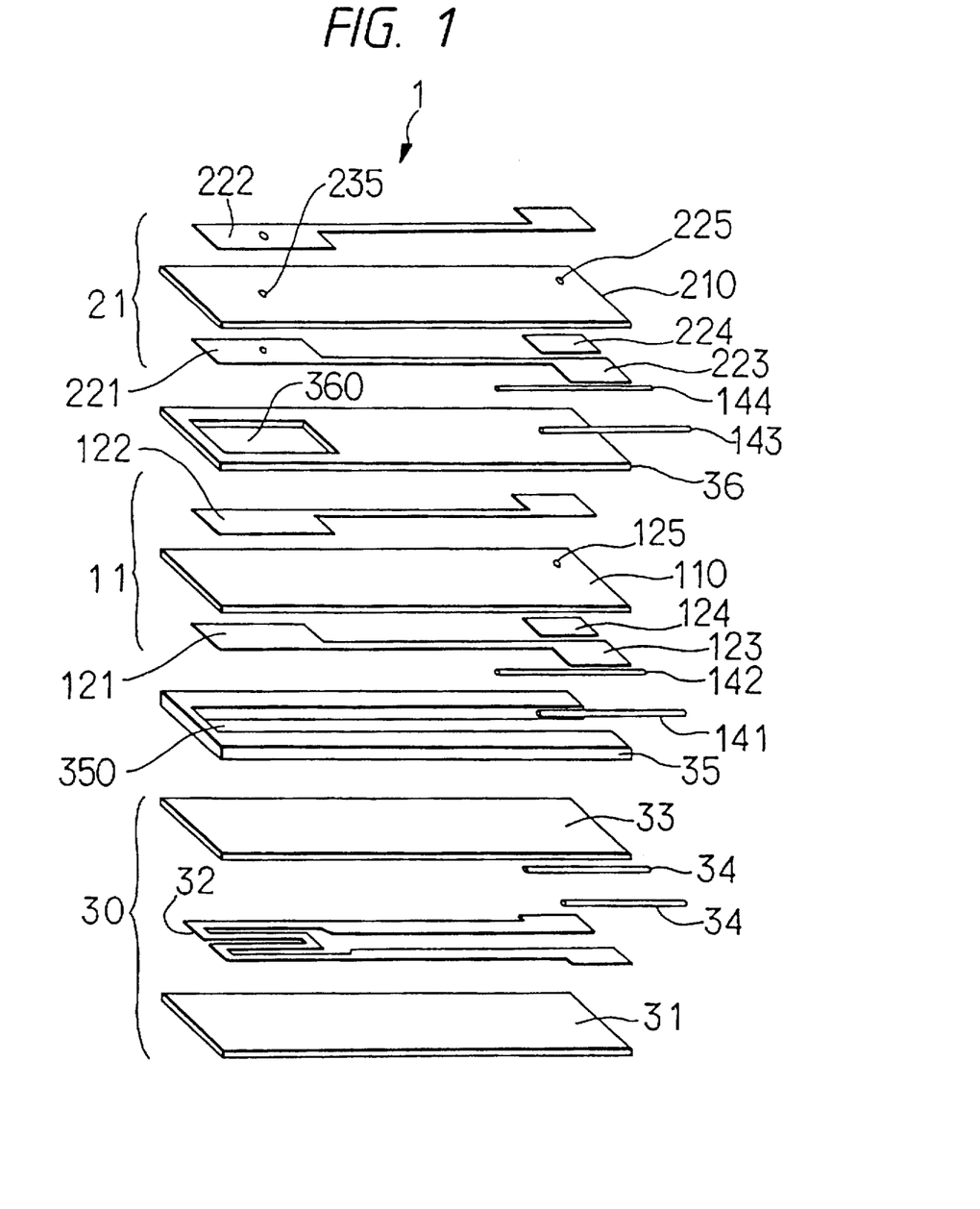
FIG. 1 is an exploded perspective view showing constituents of an air-fuel ratio sensor in accordance with a first embodiment of the present invention.
Figure 2:
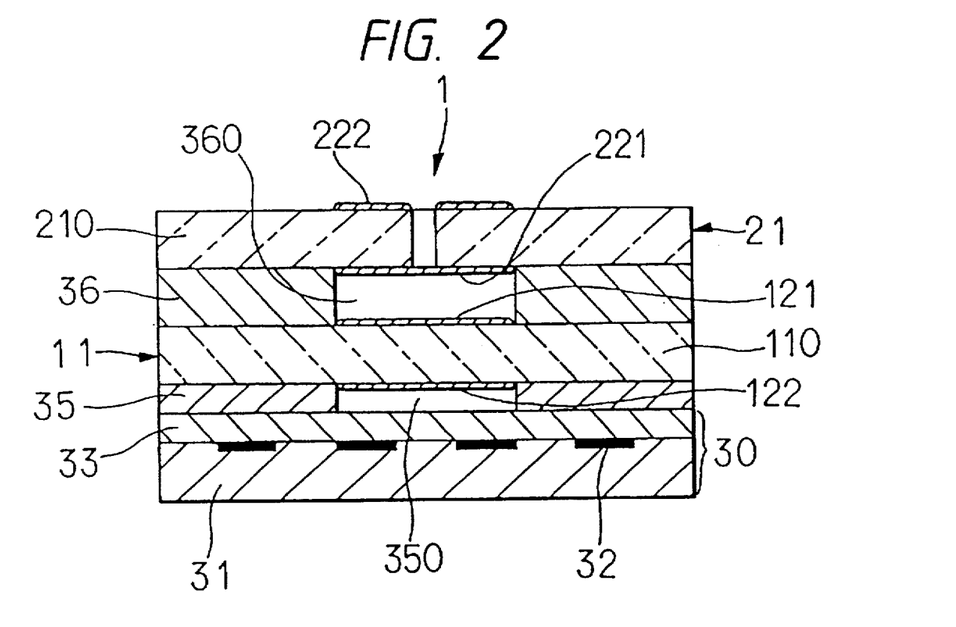
FIG. 2 is a transverse cross-sectional view showing the air-fuel ratio sensor in accordance with the first embodiment of the present invention.

As shown in FIGS. 1 and 2, an air-fuel ratio sensor 1 of the first embodiment of the present invention chiefly comprises a platelike reaction section made of solid electrolyte for detection of oxygen concentration and a heater section. The reaction section is separated into a sensing cell 11 and a pumping cell 21. The heater section is constituted by a heater sheet 30 that generates a sufficient amount of heat to increase the temperature of the reaction section (11 and 21). Sensing cell 11, pumping cell 21 and heater sheet 30 cooperatively construct a multiple layer structure (or a laminated layer structure). Spacers are adequately interposed between these layers.

The heater sheet 30 comprises a platelike insulating sheet 31 chiefly containing at least one component selected from the group consisting of α-alumina, steatite and mullite. A filmy resistance element 32 is provided on the platelike insulating sheet 31. A member covering the resistance element 32 entirely and hermetically is another platelike insulating sheet 33 chiefly containing at least one component selected from the group consisting of α-alumina, steatite and mullite. A resistance-temperature coefficient inherent to the resistance element 32 is within a range of $0.5 \times 10^3$ to $2.0 \times 10^3$ ppm/°C. as indicated by two inclined straight lines 61 and 62 shown in FIG. 4. The resistance element 32 is made of a cermet containing Pt—Pd group alloy and alumina.

The sensing cell 11, as shown in FIGS. 1 and 2, comprises a platelike sheet 110 of solid electrolyte (zirconia) and a pair of sensing electrodes 121 and 122 disposed on opposed surfaces of the solid electrolyte sheet 110. Sensing electrodes 121 and 122 cooperatively produce a signal representing a detected oxygen concentration (i.e., a cell electromotive force of oxygen). One electrode (measuring electrode) 122 is electrically connected with a terminal pattern 124 disposed on the opposed surface of the solid electrolyte sheet 110 via a through hole 125 or conductor. The terminal pattern 124 and the other electrode (referential electrode) 121 are arranged on the same surface of the solid electrolyte sheet 110 but are spaced from each other. These electrodes 121 and 122 are electrically connected to leads 141 and 142 via terminal patterns 123 and 124, respectively. Leads 141 and 142 are firmly held between a U-shaped ceramic sheet 35 and solid electrolyte sheet 110.

The pumping cell 21 comprises a platelike sheet 210 of solid electrolyte (zirconia) and a pair of pumping electrodes 221 and 222 disposed on opposed surfaces of the solid electrolyte sheet 210. Pumping electrodes 221 and 222 cooperatively act to shift oxygen ions to the surfaces of the solid electrolyte sheet 210. As shown in FIG. 1, one pumping electrode 222 is electrically connected with a terminal pattern 224 disposed on the opposed surface of the solid electrolyte sheet 210 via a through hole 225 or conductor.

The terminal pattern 224 and the other pumping electrode 221 are arranged on the same surface of the solid electrolyte sheet 210 but are spaced from each other. These pumping electrodes 221 and 222 are electrically connected to leads 143 and 144 via terminal patterns 223 and 224, respectively. Leads 143 and 144 are firmly held between a ceramic sheet 36 and the solid electrolyte sheet 210.

The ceramic sheet 36 has an opening that serves as a measured gas chamber 360 as shown in FIG. 2. The other ceramic sheet 35 has an opening that serves as a referential chamber 350 as shown in FIG. 2. Atmospheric air is introduced into this referential chamber 350. These ceramic sheets 35 and 36 serve as spacers between interposed the stacked or laminated layers of pumping cell 21, sensing cell 11 and heater sheet 30.

The heater sheet 30, disposed on an opposite surface of the ceramic sheet 35, comprises a resistance element 32 printed on the insulating sheet 31. The resistance element 32 is a resistive heater element having a resistance-temperature coefficient equal to or smaller than $2.0 \times 10^3$ ppm/°C. The resistance element 32 is connected to leads 34 held between the insulating cover 33 and the insulating sheet 31.

Figure 5:
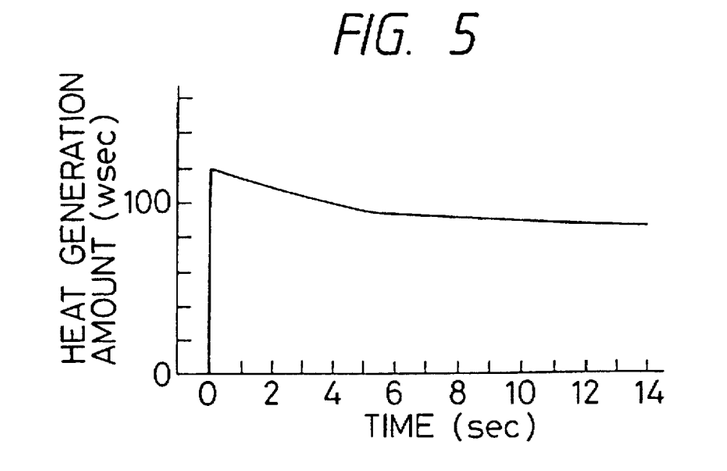
FIG. 5 is a view showing a change in the heat generation for an air-fuel ratio sensor using a resistance element formed by using a "type A" paste in accordance with the first embodiment of the present invention.

When a constant voltage is applied, a heat generation amount of the resistance element 32 can be maintained at a constant level due to its adequate resistance-temperature coefficient as shown in FIG. 5. The heat generation amount is slightly decreased due to change of the resistance value (i.e., self heat generation), but is not serious and negligible. The air-fuel ratio sensor 1 is heated by this resistance element 32, and the temperature of this air-fuel ratio sensor 1 increases as shown in FIG. 6.

Figure 6:
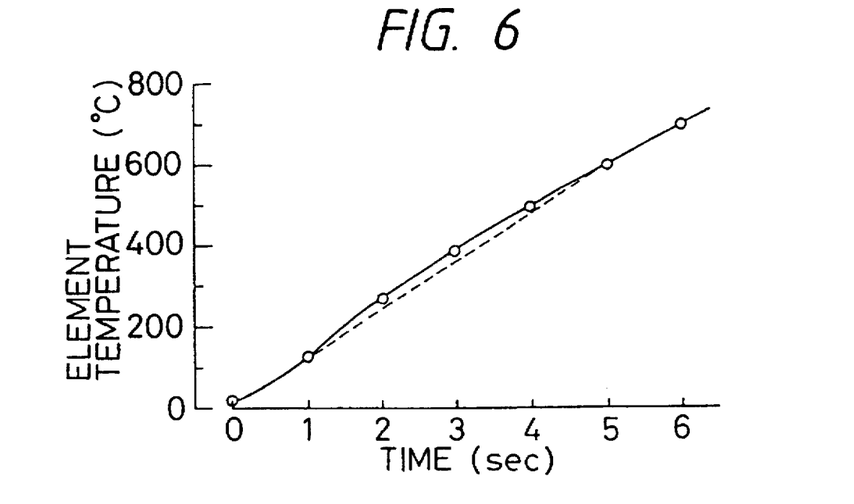
FIG. 6 is a view showing a temperature change of the air-fuel ratio sensor using the resistance element based on the "type A" paste in accordance with the first embodiment of the present invention.

As apparent from FIG. 6, the temperature gradient (°C./sec) is substantially constant irrespective of an elapsed time during the temperature increase of the sensor element. The sensor element and the heater sheet are not subjected to a severe thermal stress. This is desirable in guaranteeing the durability of insulating sheets 31 and 33.

Manufacturing processes for the above-described air-fuel ratio sensor 1 will be explained hereinafter.

First, a method for manufacturing a zirconia raw sheet used for both the sensing cell 11 and the pumping cell 21 will be explained.

A ceramic mixture is prepared. This ceramic mixture comprises yttria-partially-stabilized zirconia of 100 weight part, α-alumina of 1 weight part, PVB (polyvinyl butyral of 5 weight part, DBP (dibutyl phthalate) of 10 weight part, ethanol of 10 weight part, and toluene of 10 weight part. The yttria-partially-stabilized zirconia, serving as a main component of the ceramic mixture, has a mean particle radius of 0.5 μm and a mixture ratio of 6 mol % yttria and 94 mol % zirconia.

The ceramic mixture is uniformly mixed in a ball mill. The slurry of thus-milled ceramic mixture is formed with a doctor-blade method into a sheet having a thickness of 0.3 mm in a dried condition.

The obtained sheet compact is cut into a rectangular sheet of 5×70 mm. Through hole 215 is formed on the rectangular sheet. Then, measuring electrode 122, referential electrode 121, and terminal patterns 123 and 124 are formed with a screen printing method using a platinum (Pt) paste. Thus, a raw sheet for sensing cell 11 is fabricated.

In the same manner, the above-described sheet compact is cut into a rectangular sheet of 5×70 mm. A through hole 235, having a diameter of 0.5 φ, is opened at a predetermined position of the rectangular sheet. Measured gas is introduced through this through hole 235. Through hole 225 is formed on the rectangular sheet. Then, pumping electrodes 222 and 221 and terminal patterns 223 and 224 are formed on the rectangular sheet by a screen printing method using a platinum (Pt) paste. Thus, a raw sheet for pumping cell 21 is fabricated.

Next, a manufacturing method for an alumina raw sheet will be explained. The alumina raw sheet is used to fabricate each of ceramic sheets 35 and 36, insulating sheet 31 and insulating cover 33.

A ceramic mixture is prepared. This ceramic mixture comprises α-alumina of 98 weight part, 6 mol % yttria-partially-stabilized zirconia of 3 weight part, PVB (polyvinyl butyral of 10 weight part, DBP (dibutyl phthalate) of 10 weight part, ethanol of 30 weight part, and toluene of 30 weight part. The α-alumina, serving as a main component of the ceramic mixture, has a mean particle radius of 0.3μm.

This ceramic mixture is uniformly mixed in a ball mill. The slurry of thus-milled ceramic mixture is formed with a doctor-blade method into a sheet having a thickness of 0.3 mm in a dried condition.

The obtained sheet compact of 0.3 mm thick is cut into a rectangular sheet of 5×70 mm. The resistance element 32 is printed on the rectangular sheet by a screen printing method using a paste. This paste is either a "type A" paste or a "type B" paste. "Type A" paste contains platinum (Pt) and palladium (Pd) specified by a weight ratio of 3:1 with alumina of 10 wt %. "Type B" paste contains platinum (Pt) and palladium (Pd) specified by a weight ratio of 9:1 with alumina of 10 wt %. Thus, a raw sheet for heater sheet 30 is fabricated.

The printing region of resistance element 32 entirely encompasses the projected regions of electrodes 121 and 122 of sensing cell 11 and electrodes 221 and 222 of pumping cell 21. For example, the resistance value of resistance element 32 is 2.0 Ω between its terminals.

The above-described sheet compact is cut into a rectangular sheet of 5×70 mm, as a raw sheet for insulating cover 33 of heater sheet 30.

For the ceramic sheet 36 sandwiched between sensing cell 11 and pumping cell 21, the above-described sheet compact of 0.3 mm thick is cut into a rectangular sheet of 5×70 mm. A rectangular hole, serving as measured gas chamber 360, is opened at a predetermined portion of this rectangular sheet. Thus, a raw sheet for ceramic sheet 36 is fabricated.

On the other hand, for the ceramic sheet 35 sandwiched between sensing cell 11 and heater sheet 30, a sheet compact of 0.5 mm thick is manufactured by the same manufacturing method as the above-described sheet compact of 0.3 mm. This sheet compact of 0.5 mm thick is cut into a rectangular sheet of 5×70 mm. A rectangular region equivalent to 2×65 mm is cut and removed from the one side closer to the leads. As a result, the U-shaped raw sheet for ceramic sheet 35 is left. The resultant rectangular cutout of 2×65 mm defines the referential gas chamber 350.

Leads 141 to 144 are 7 m long and made of 13% Rh—Pt wire of 0.2φ. Above-explained raw sheets (i.e., so-called "green sheets") and leads 141–144 are stacked successively according to a predetermined order to constitute a multilayer structure shown in FIG. 1 by using a paste serving as a pressure sensitive adhesive at an ordinary temperature. The multilayered assembly is pressed and fixed firmly. Then, the multilayered assembly is sintered at 1,500° C. for one hour, thereby forming the main body of the air-fuel ratio sensor 1 of the first embodiment.

Figure 4:
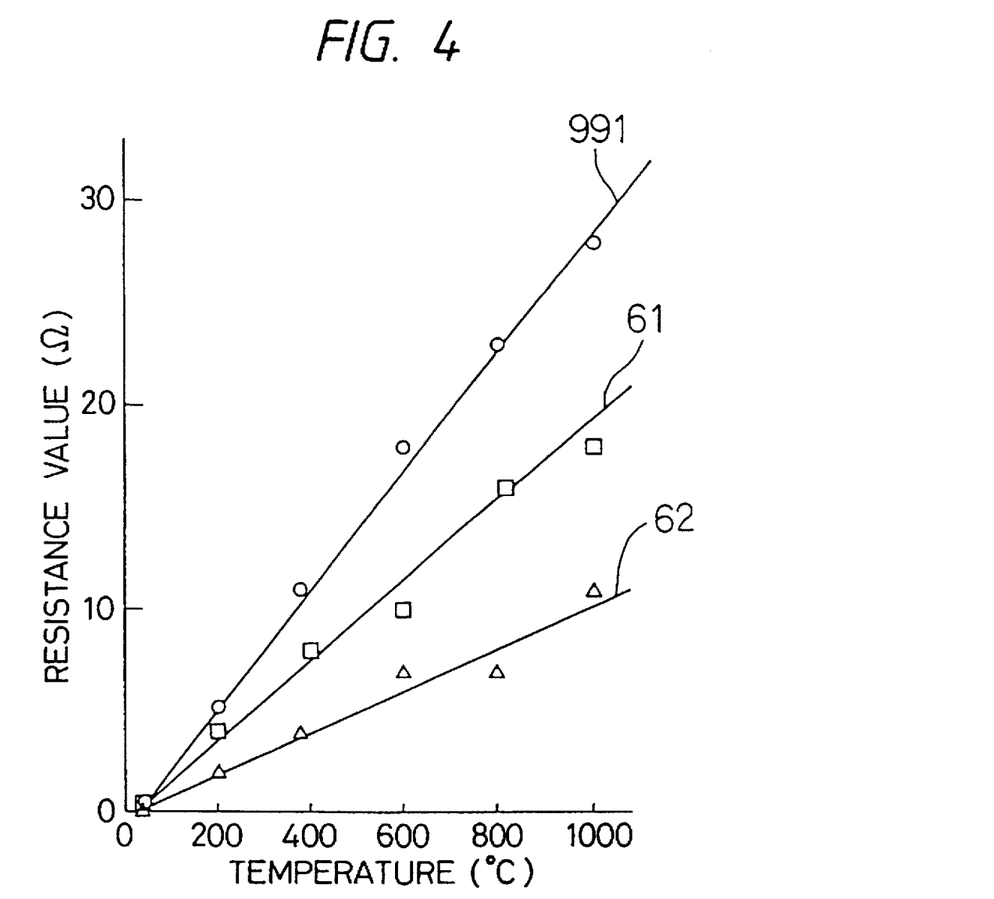
FIG. 4 is a graph showing a resistance value change of the air-fuel ratio sensor in accordance with the first embodiment of the present invention.

An experiment is conducted to evaluate the properties of the air-fuel ratio sensor 1 of the first embodiment. To obtain an objective evaluation, a comparative air-fuel ratio sensor is prepared in this experiment. The comparative air-fuel ratio sensor comprises a resistance element formed by using a "type M" paste containing Pt and 10 wt % alumina. Other arrangements of the comparative air-fuel ratio sensor are identical with those of the air-fuel ratio sensor 1 of the first embodiment. A straight line 991 shown in FIG. 4 represents a resistance-temperature coefficient of the comparative air-fuel ratio sensor.

Resistance-temperature coefficients of the experimented air-fuel ratio sensors are measured in accordance with a method described below.

To measure the resistance-temperature coefficients, three kinds of pastes "type A", "type B" and "type M" are prepared. As described above, "type A" paste contains platinum (Pt) and palladium (Pd) by a weight ratio of 3:1 and 10 wt % alumina. "Type B" paste contains platinum (Pt) and palladium (Pd) by a weight ratio of 9:1 and 10wt % alumina. And, "type M" paste contains Pt and 10wt % alumina. Three kinds of resistance elements are formed by screen printing the pastes "type A", "type B" and "type M" on the insulating sheet 31, respectively. The resistance value of each resistance element is set to the previously described value. Thus, a total of three kinds of resistance element sheets are prepared as samples for comparison.

Figure 7:
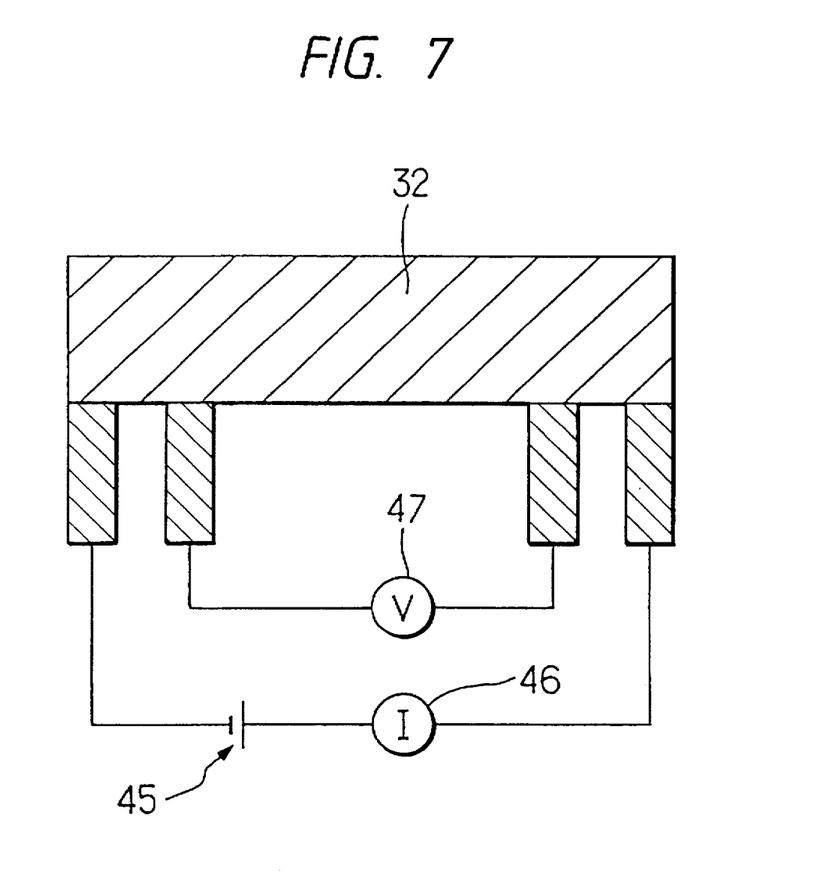
FIG. 7 is a diagram showing a resistance measuring circuit for the resistance element in accordance with the first embodiment of the present invention.

Pt leads are connected to each sample to measure a resistance-temperature coefficient. Then, the sample is placed in an electric furnace having a setting temperature arbitrarily variable. As shown in FIG. 7, an electric voltage is applied from electric power source 45 to the resistance element 32. A potentiometer 47 measures a potential difference between the terminals of resistance element 32. An ammeter 46 measures current flowing through resistance element 32. Thus, the resistance value of each sample is obtained based on both the measured potential difference and the measured current. The experimental result is plotted in FIG. 4. In FIG. 4, straight line 991 represents the comparative resistance element (i.e., "type M" paste). Straight line 61 represents the resistance element of "type A" paste in accordance with the first embodiment of the present invention. Straight line 62 represents the resistance element of "type B" paste in accordance with the first embodiment of the present invention.

The resistance-temperature coefficient is calculated from the following equation.

$$K_{RT}\ (ppm/^\circ C.) = \{(R_{1000}-R_{20})/R_{20}\} \div (1,000-20) \times 10^6$$

where $K_{RT}$ represents the resistance-temperature coefficient, $R_{1000}$ represents a resistance value at a temperature 1,000° C., and $R_{20}$ represents a resistance value at a temperature 20° C.

Table 1 shows a calculation result.

TABLE 1

|  | $K_{RT}$ (ppm/°C.) |
|---|---|
| Emb. 1-1 (paste A) | $1.1 \times 10^3$ |
| Emb. 1-2 (paste B) | $2.0 \times 10^3$ |
| Comp. (paste M) | $3.1 \times 10^3$ |

An experimental result relating to the correlation between an activation time of an air-fuel ratio sensor and damage of a sensor element will be explained.

Figure 3:
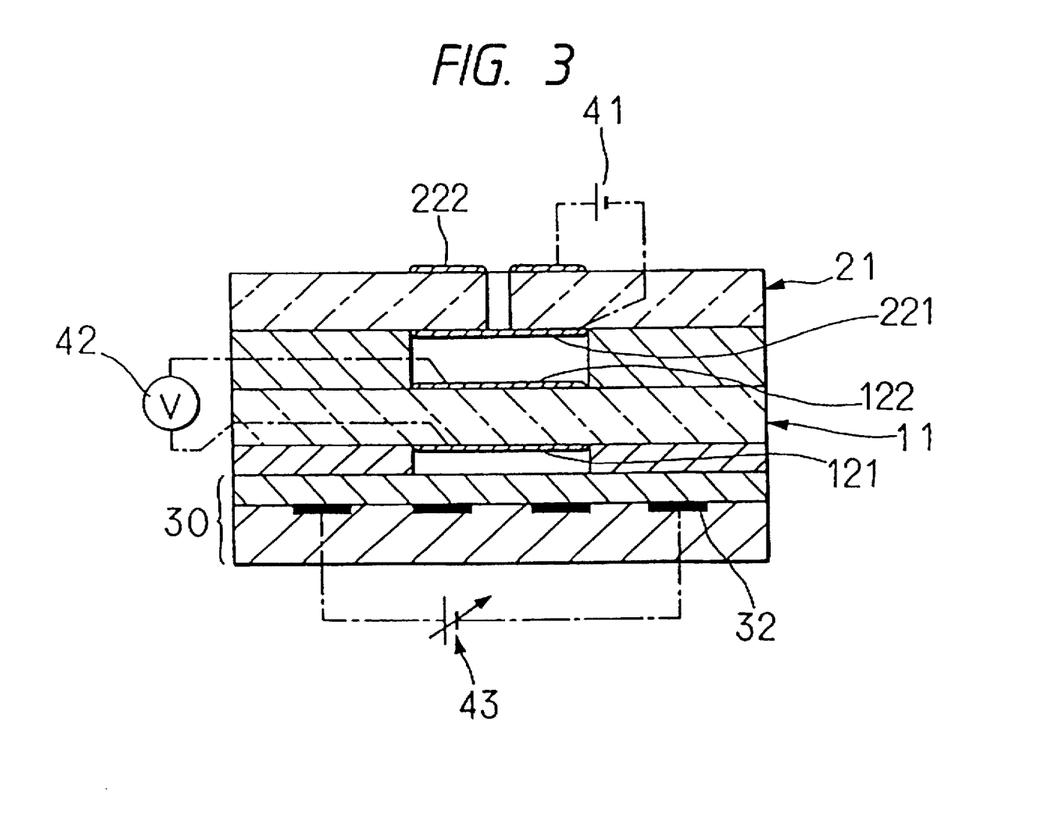
FIG. 3 is a view showing a circuit that measures a temperature increase in the air-fuel ratio sensor in accordance with the first embodiment of the present invention.

The experiment was conducted at a temperature of 20° C. Each air-fuel ratio sensor is exposed in a nitrogen gas atmosphere comprising 5% oxygen gas. As shown in FIG. 3, a DC voltage of 1 V is applied between electrodes 221 and 222 of pumping cell 21 from a DC power source 41, to pump oxygen into the measured gas chamber 360 and to pump out the same to the outside space. A DC potentiometer 42 is connected between electrodes 121 and 122 of sensing cell 11 to measure an output voltage of the sensing cell 11.

An arbitrary voltage is applied to the resistance element 32 from a variable DC stabilizing power source 43.

The temperature of heater sheet 30 is measured by a thermocouple thermometer (not shown). The voltage application to the resistance element 32 is stopped at the moment the temperature of heater sheet 30 has reached 70° C. This is to prevent the sensor element from being damaged due to unpredictable factors other than the thermal stress during temperature increase.

To judge whether the air-fuel ratio sensor is active, a voltage is simultaneously applied to the resistance element 32 and the pumping cell 21. At the time the output voltage of sensing cell 11 becomes 0.45 V, a judgement is made that the sensor is activated sufficiently. This time is referred to as an activation time.

The presence of element damage (cracks) is checked by dyeing the tested element by dyestuff. A peculiar color change is recognized along a crack if there is any crack.

Table 2 shows an experimental result.

TABLE 2

|  | Activation Time (sec) | | | | | | | |
|---|---|---|---|---|---|---|---|---|
|  | 3 | 4 | 5 | 6 | 7 | 8 | 9 | 10 |
| Emb.1-1(paste A) | x | o | o | o | o | o | o | o |
| Emb.1-2(paste B) | x | x | o | o | o | o | o | o |
| Comp.(paste M) | x | x | x | x | x | x | o | o |

As understood from table 2, the air-fuel ratio sensor using the "type M" paste causes a crack (as indicated by x in table 2) when the activation time is set to five seconds. Accordingly, the comparative sample cannot clear the required standard of five second warmup ability. However, the air-fuel ratio sensor using the "type A" paste and the air-fuel ratio sensor using the "type B" paste do not cause any crack (as indicated by o in table 2) when the activation time is set to five seconds. Accordingly, the samples of the first embodiment can clear the required standard of five second warmup ability.

As understood from tables 1 and 2, the air-fuel ratio sensor 1 of the first embodiment can be activated without causing any cracks during five seconds when the resistance element has a resistance-temperature coefficient equal to or smaller than $2.0 \times 10^3$ ppm/°C.

From the view point of thermal stress, having a smaller resistance-temperature coefficient is preferable. The temperature of the sensor element needs to be measured based on the resistance-temperature coefficient. From the view point of measuring sensitivity, having a positive and larger resistance-temperature coefficient is preferable to improve the accuracy of the control of the temperature of the resistance element. To satisfy both the requirements of thermal stress and measuring sensitivity, the resistance-temperature coefficient equal to or more than $0.5 \times 10^3$ ppm/°C. is preferable.

Second Embodiment

A second embodiment provides an air-fuel ratio sensor different from the air-fuel ratio sensor 1 of the first embodiment in that the paste for resistance element 32 is modified.

More specifically, various samples (cermets) for resistance element 32 used in the second embodiment are prepared by changing the ratio of the primary component (i.e., Pt) and the secondary component (Rh, Pd and Ir) as shown in table 3.

The correlation between an activation time of an air-fuel ratio sensor and damage of a sensor element is obtained experimentally with the same method used in the first embodiment. Furthermore, the resistance-temperature coefficient of each sample is measured.

Table 3 shows an experimental result showing the correlation between the activation time of each air-fuel ratio sensor and damage of its sensor element. Table 4 shows a measured resistance-temperature coefficient of each sample.

TABLE 3

| | ratio of Pt/ secondary component | Activation Time (sec) | | | | | | | |
|---|---|---|---|---|---|---|---|---|---|
| | | 3 | 4 | 5 | 6 | 7 | 8 | 9 | 10 |
| Pd | 9/1 | x | x | o | o | o | o | o | o |
| | 3/1 | x | o | o | o | o | o | o | o |
| | 3/2 | x | x | o | o | o | o | o | o |
| Rh | 9/1 | x | o | o | o | o | o | o | o |
| Ir | 9/1 | x | o | o | o | o | o | o | o |
| | 3/1 | x | x | o | o | o | o | o | o |
| | 3/2 | x | x | x | o | o | o | o | o |

TABLE 4

| | ratio of Pt/ secondary component | $K_{RT}$ (ppm/°C.) |
|---|---|---|
| Pd | 9/1 | $2.0 \times 10^3$ |
| | 3/1 | $1.0 \times 10^3$ |
| | 3/2 | $1.8 \times 10^3$ |
| Rh | 9/1 | $1.2 \times 10^3$ |
| Ir | 9/1 | $1.3 \times 10^3$ |
| | 3/1 | $1.1 \times 10^3$ |
| | 3/2 | $2.3 \times 10^3$ |

As understood from table 3, all of tested samples except for the air-fuel ratio sensor with Pt/Ir of 3:2 can clear the required standard of five second warmup ability.

From table 4, the air-fuel ratio sensor of the second embodiment can be activated without causing any cracks during five seconds when the resistance element has a resistance-temperature coefficient equal to or smaller than $2.0 \times 10^3$ ppm/°C.

Among the above-described secondary components Rh, Pd and Ir, Pd and Rh are preferable in their excellent durability.

Other components preferably adopted as the secondary component of the second embodiment of the present invention are, for example, Pt group elements including Ru and Os.

Other material preferable for the insulating sheet is a ceramic having a thermal expansion coefficient similar to α-alumina, steatite and mullite disclosed in the above-described embodiments.

Furthermore, α-alumina used in the above-described embodiments as a material for the alumina insulating sheet can be replaced by γ-alumina.

As this invention may be embodied in several forms without departing from the spirit of essential characteristics thereof, the present embodiments as described are therefore intended to be only illustrative and not restrictive, since the scope of the invention is defined by the appended claims rather than by the description preceding them, and all changes that fall within the metes and bounds of the claims, or equivalents of such metes and bounds, are therefore intended to be embraced by the claims.

What is claimed is:

1. An air-fuel ratio sensor comprising:
   a platelike oxygen sensing section made of a solid electrolyte;
   a heater sheet heating said oxygen sensing section;
   said oxygen sensing section and said heater sheet being stacked with intervening spacers to constitute a multi-layer construction, wherein
   said heater sheet comprises:
   a first platelike insulating sheet chiefly containing at least one component selected from the group consisting of α-alumina, steatite and mullite;
   a filmy resistance element disposed on said first insulating sheet and having a resistance-temperature coefficient within a range of $0.5 \times 10^3$ to $2.0 \times 10^3$ ppm/°C.; and
   a second platelike insulating sheet covering said resistance element and chiefly containing at least one component selected from the group consisting of α-alumina, steatite and mullite.

2. The air-fuel ratio sensor in accordance with claim 1, wherein said resistance element is made of a cermet comprising a primary component of Pt and a secondary component selected from the group consisting of Rh, Pd and Ir.

3. The air-fuel ratio sensor in accordance with claim 1, wherein the resistance element is made of a cermet comprising a primary component of Pt and a secondary component selected from the group consisting of Ru and Os.

4. A heater sheet for an air-fuel ratio sensor having an oxygen sensing section, the heater sheet comprising:
   a first insulating sheet;
   a resistance element disposed on said first insulating sheet and having a resistance-temperature coefficient equal to or smaller $2.0 \times 10^3$ ppm/°C.; and
   a second insulating sheet covering said resistance element.

5. The heater sheet in accordance with claim 4, wherein said resistance element has a resistance temperature coefficient within a range of $0.5 \times 10^3$ to $2.0 \times 10^3$ ppm/°C.

6. The heater sheet in accordance with claim 4, wherein said resistance element comprises a cermet including a primary component of Pt and a secondary component selected from the group consisting of Rh, Pd, Ir, Ru, and Os.

7. The heater sheet in accordance with claim 4, wherein said resistance element is capable of reaching a predetermined active temperature within a predetermined startup period.

8. The heater sheet in accordance with claim 7, wherein said active temperature is approximately 600° C.

9. The heater sheet in accordance with claim 7, wherein said startup period is approximately five seconds.

10. The heater sheet in accordance with claim 5, wherein the temperature of said resistance element is controlled by monitoring of the resistance value of said resistance element by the sensor.

11. The heater sheet in accordance with claim 4, wherein said first and second insulating sheets each comprise a ceramic.

12. The heater sheet in accordance with claim 4, wherein said first and second insulating sheets each chiefly contain at least one component selected from the group consisting of α-alumina, γ-alumina, steatite, and mullite.

13. A method for sensing an air-fuel ratio of an internal combustion engine with an oxygen sensing section, comprising:

warming the oxygen sensing section by heating a heater sheet to a predetermined active temperature, the heater sheet including a first insulating sheet chiefly containing at least one component selected from the group consisting of α-alumina, γ-alumina, steatite, and mullite, a resistance element disposed on said first insulating sheet and having a ' resistance-temperature coefficient equal to or smaller than $2.0 \times 10^3$ ppm/°C., and a second insulating sheet covering said resistance element and chiefly containing at least one component selected from the group consisting of α-alumina, γ-alumina, steatite, and mullite;

maintaining the temperature of the resistance element at approximately the active temperature;

sensing the oxygen content of the exhaust gas of the engine with the oxygen sensing section; and comparing the sensed oxygen content with the oxygen content of a reference gas.

14. The method in accordance with claim 13, wherein the active temperature is approximately 600°C.

15. The method in accordance with claim 13, further including the step of monitoring the temperature of the resistance element by detecting the resistance value of the resistance element, and wherein the resistance element has a resistance-temperature coefficient within a range of $0.5 \times 10^3$ to $2.0 \times 10^3$ ppm/°C.

* * * * *